US010876168B2

(12) United States Patent
Zou et al.

(10) Patent No.: US 10,876,168 B2
(45) Date of Patent: Dec. 29, 2020

(54) MOLECULAR DETECTION/DIAGNOSIS REAGENT FOR TUMOR

(71) Applicant: CREATIVE BIOSCIENCES (GUANGZHOU) CO., LTD., Guangzhou (CN)

(72) Inventors: Hongzhi Zou, Guangzhou (CN); Feng Niu, Guangzhou (CN); Shan Wu, Guangzhou (CN); Rongsong Zhao, Guangzhou (CN); Hao Yu, Guangzhou (CN)

(73) Assignee: CREATIVE BIOSCIENCES (GUANGZHOU) CO., LTD., Guangdong (CN)

(*) Notice: Subject to any disclaimer, the term of this patent is extended or adjusted under 35 U.S.C. 154(b) by 3 days.

(21) Appl. No.: 16/067,314

(22) PCT Filed: Dec. 13, 2016

(86) PCT No.: PCT/CN2016/109622
§ 371 (c)(1),
(2) Date: Jun. 29, 2018

(87) PCT Pub. No.: WO2017/114150
PCT Pub. Date: Jul. 6, 2017

(65) Prior Publication Data
US 2019/0010557 A1 Jan. 10, 2019

(30) Foreign Application Priority Data
Dec. 31, 2015 (CN) .......................... 2015 1 1034264

(51) Int. Cl.
*C12Q 1/6886* (2018.01)
*C12N 15/11* (2006.01)
*B03C 1/015* (2006.01)
*C12Q 1/6806* (2018.01)
*C12Q 1/6853* (2018.01)
*C12Q 1/686* (2018.01)

(52) U.S. Cl.
CPC ............ *C12Q 1/6886* (2013.01); *B03C 1/015* (2013.01); *C12N 15/11* (2013.01); *C12Q 1/6806* (2013.01); *C12Q 1/6853* (2013.01); *C12Q 1/686* (2013.01); *C12Q 2600/112* (2013.01); *C12Q 2600/118* (2013.01); *C12Q 2600/154* (2013.01); *C12Q 2600/166* (2013.01)

(58) Field of Classification Search
None
See application file for complete search history.

(56) References Cited

U.S. PATENT DOCUMENTS

| 2005/0239086 A1* | 10/2005 | Lipkin ................. C12Q 1/6837 435/6.1 |
| 2012/0264640 A1 | 10/2012 | An et al. |
| 2016/0040244 A1 | 2/2016 | An et al. |
| 2016/0153050 A1* | 6/2016 | An ....................... C12Q 1/6886 506/9 |

FOREIGN PATENT DOCUMENTS

| CN | 102686744 A | 9/2012 |
| CN | 103314114 A | 9/2013 |
| CN | 104812899 A | 7/2015 |
| CN | 105543354 A | 5/2016 |
| JP | 2013-509872 A | 3/2013 |
| WO | 2014/073785 A1 | 5/2014 |
| WO | 2015/023146 A1 | 2/2015 |
| WO | 2015/132273 A1 | 9/2015 |
| WO | 2015/153283 A1 | 10/2015 |

OTHER PUBLICATIONS

Oh (The Journal of Molecular Diagnostics vol. 15 No. 4 Jul. 2013).*
Communication, dated Jul. 26, 2019, issued by the European Patent Office in Application No. 16880940.8.
Ahlquist, David A., et al., "Next-generation stool DNA test accurately detects colorectal cancer and large adenomas", Gastroenterology, vol. 142, No. 2, pp. 248-256, Feb. 2012, 10 pages total.
Communication, dated Jan. 10, 2019, issued by the Intellectual Property Office of Australia in application No. 2016383317.
Communication, dated Mar. 7, 2019, issued by the Canadian Intellectual Property Office in application No. 3,010,143.
Communication, dated Jun. 4, 2019, issued by the Japanese Patent Office in application No. 2018-533781.
Taejeong OH et al., "Genome-Wide Identification and Validation of a Novel Methylation Biomarker, SDC2, for Blood-Based Detection of Colorectal Cancer", The Journal of Molecular Diagnostics, Jul. 2013, 10 pages, vol. 15, No. 4.
Xin Huang et al., "Prognostic significance of altered expression of SDC2 and CYR61 in esophageal squamous cell carcinoma", Oncology Reports, Dec. 31, 2009, pp. 1123-1129, vol. 21.
Melina-Theoni Gyparaki et al., "DNA methylation biomarkers as diagnostic and prognostic tools in colorectal cancer", Journal of Molecular Medicine, Sep. 21, 2013, pp. 1249-1256, vol. 91.
Meng Xue et al., "Value of DNA methylation markers in colorectal cancer screening", World Chinese Journal of Digestology, Oct. 18, 2015, pp. 4626-4635, vol. 23, No. 29.
S. Colella et al., "Sensitive and Quantitative Universal Pyrosequencing tm Methylation Analysis of CpG Sites", Molecular Diagnostics, 2003, 4 pages, vol. 35, No. 1.

(Continued)

Primary Examiner — Amanda Haney
(74) Attorney, Agent, or Firm — Sughrue Mion, PLLC

(57) ABSTRACT

The present invention discloses a tumor molecular detection/diagnostic reagent, which takes excrement as a detection sample and includes an SDC2 gene methylation detection reagent. The methylation level of the SDC2 gene detected in the excrement has an extremely high relevance to the onset of the colorectal cancer. The sensitivity of the SDC2 gene in the excrement is 87 percent and the specificity is up to 98 percent or even higher than that in tissue.

15 Claims, 9 Drawing Sheets

Specification includes a Sequence Listing.

(56) References Cited

OTHER PUBLICATIONS

Innoc Han et al., "New insights into syndecan-2 expression and tumourigenic activity in colon carcinoma cells", Journal of Molecular Histology, 2004, pp. 319-326, vol. 35

Dean E. Brenner et al., "Fecal DNA Biomarkers for the Detection of Colorectal Neoplasia: Attractive, but Is It Feasible?", Journal of the National Cancer Institute, Aug. 3, 2005, pp. 1107-1109, vol. 97, No. 15.

Hiromu Suzuki et al., "A genomic screen for genes upregulated by demethylation and histone deacetylase inhibition in human colorectal cancer", Nature Genetics, Jun. 2002, pp. 141-149, vol. 31.

R. Salehi et al., "Methylation pattern of SFRP1 promoter in stool sample is a potential marker for early detection of colorectal cancer", Advanced Biomedical Research, Oct.-Dec. 2012, 9 pages, vol. 1, Issue 4.

Hyon K. Choi et al., "Alcohol intake and risk of incident gout in men: a prospective study", The Lancet, Apr. 17, 2004, pp. 1277-1281, vol. 363.

Office Action, issued by the Chinese Patent Office in Application No. 201511034264.X, dated Jun. 5, 2018.

International Search Report for PCT/CN2016/109622, dated Mar. 8, 2017 [PCT/ISA/210].

Communication, dated Sep. 20, 2019, issued by the Korean Intellectual Property Office in counterpart application No. 10-2018-7020424.

* cited by examiner

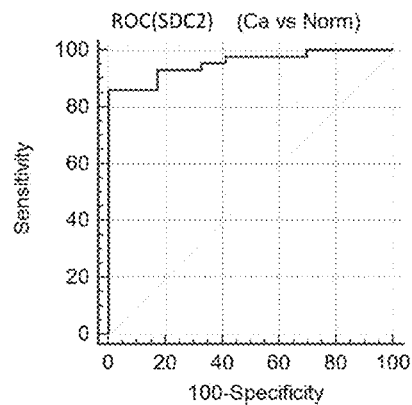
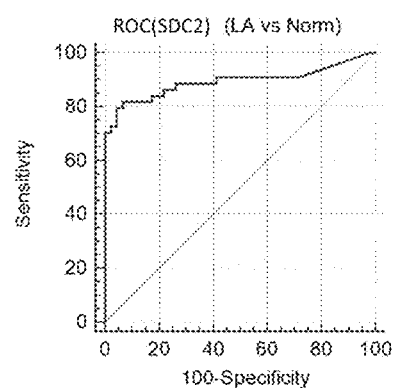
Fig. 1A                               Fig. 1B
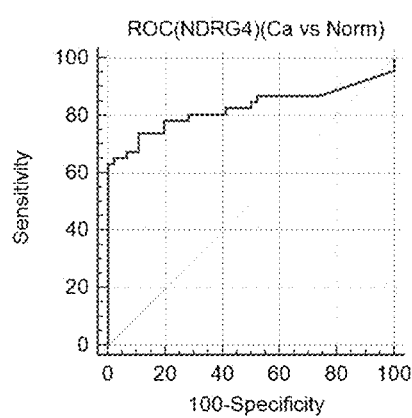
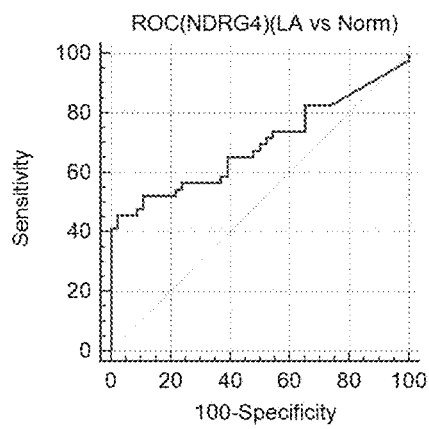
Fig. 2A                               Fig. 2B

US 10,876,168 B2

MOLECULAR DETECTION/DIAGNOSIS REAGENT FOR TUMOR

CROSS REFERENCE TO RELATED APPLICATIONS

This application is a National Stage of International Application No. PCT/CN2016/109622, filed Dec. 13, 2016, claiming priority based on Chinese Patent Application No. 201511034264.X, filed Dec. 31, 2015 and entitled "Tumor Molecular Detection/Diagnostic Reagent," the entire contents of each of which are hereby incorporated by reference.

TECHNICAL FIELD

The present invention belongs to the field of biological medicines, relates to a tumor molecular detection/diagnostic reagent, and more particularly relates to a tumor molecular detection/diagnostic reagent, which takes excrement as a detection sample.

BACKGROUND ART

At present, there are mainly two general technologies for screening colorectal cancer.

One technology is fecal occult blood testing. Generally, there are no symptoms in the early stage of intestinal cancers. Cancer cells can grow decades on the intestinal wall of a large intestine before metastasizing to other parts. Prior to any symptom onset, little blood may exudate from hyperplastic tissues, and enter excrement which will be defecated. The fecal occult blood testing is to detect blood components (hemoglobin serving as a detection object) in the excrement. If multiple continuous tests have positive reactions indicating alimentary tract hemorrhage, a further examination should be made to make sure no tumorigenesis in the intestinal tract. This method has the advantages that results can be shown quickly and clearly and semiquantitative. But it also has a series of disadvantages that: firstly, it has poor specificity and is greatly influenced by diets.

Ferrous ion-containing food and drugs may cause interference to the results, resulting in a false positive rate of 30 percent. It instructs that a patient should not take ferralia, animal blood, livers, lean and a large number of green vegetables 3 days before the occult blood testing. If a patient has bleeding gums and swallows bloody saliva carelessly, a false positive result may occur in the fecal occult blood testing. Secondly, only if the bleeding amount is more than 90 ug/ml, the method can detect occult blood due to its low sensitivity; and thirdly, the method has many limiting conditions: a patient should take a long time to do preparations in advance; because of different test parts, different response times and different judgments on development, errors may also be caused in the test of the same method, so that for general tests, it will require the patient to sample excrement in different days for continuous testing.

The other method is enteroscopy. At the present, the enteroscopy is the most effective and reliable diagnostic method for intestinal lesions. Most of patients suffering from early intestinal cancers can be detected and definitely diagnosed by an endoscope. The endoscope, inserted through the anus, can examine the rectum, the sigmoid colon, the descending colon, the transverse colon, ascending colon, the cecum and a bit of small intestine (the ileocecal tail end) connected with the large intestine. By the endoscope, a doctor can clearly find out the intestinal lesions and treat part of the intestinal lesions, for example: directly excising benign lesions such as colorectal polyps under the endoscope, performing endoscopic hemostasis on intestinal tract bleeding and clearing away foreign matters in the large intestine. The enteroscopy technology is an irreplaceable main method at the present, and is the most effective and reliable diagnostic method for the intestinal lesions. However, it also has a series of disadvantages that: firstly, preparations before examination are required: before the enteroscopy, a patient should eat fluid or low-residue semifluid food three days before examination; on the day of examination, the patient should not eat any food in the morning, and should take catharsis agents such as mannitol, generally up to 2 L, to cleanse the intestinal tract on the day before the examination day. Cleansing enema may guarantee the cleanness of the intestinal tract, and then the patient is not allowed to eat food.

During examination, the doctor will inject a certain amount of air into the enteric cavity through the enteroscope to expand the intestinal tract for observation. As the colon twists and turns, a person undergoing examination may suffer a swelling pain or have a pull feeling to different extents during examination. For people who are under great stress or suffer from severe intestinal spasm, sedatives or spasmolysis drugs are used. Non-cooperative children should be examined with the help of anesthesia. Secondly, it has an extremely high requirement for the operation proficiency level of a doctor as a beginner would easily omit diseased regions under the enteroscope, leading to missed diagnosis. Injection of the air during examination will increase the pressure in the intestine, which may easily cause perforation. Thirdly, the examination is energy-consuming and time-consuming, which causes certain pain to the patient. Furthermore, with high examination cost, this method is relatively hard to popularize in a large scale.

Besides the above-mentioned two methods, a molecular diagnostic method is a cancer diagnostic method developed fast in recent years. It is initially estimated that 130 or more types of colorectal cancer molecular markers in tissue and blood samples have been researched and reported.

As tissue sampling will cause serious trauma, researches focusing on screening of colorectal cancer markers in an excrement sample have been made. For example, Wu Yong and et al. have tried to make combined diagnosis by detecting markers such as APC, K-ras and p53 in excrement and adopting FOBT (Fecal Occult Blood Testing).

However, on one hand, excrement contains various enzymes which may digest and degrade DNA falling into the excrement; on the other hand, the excrement contains complicated components and excessive interference components, so that detection results are generally unsatisfactory. For the same target gene, its detection sensitivity and specificity in the excrement sample are much lower than those in a tissue sample, which seriously affects the judgment on results. For example, the sensitivity to colorectal cancer of the vimentin genein tissue is 83.0 percent, but will be reduced to 46 percent in excrement (J Natl Cancer Inst. 2005 Aug. 3; 97(15):1124-32); the SFRP1 and SFRP2 genes have extremely high specificity and sensitivity for colorectal cancer in the tissue; for the SFRP1 gene in the tissue, the specificity is 100 percent, and the sensitivity is 95.1 percent (Nat Genet. 2002 June; 31(2): 141-9), but in the excrement, the sensitivity is reduced to 52 percent (Adv Biomed Res. 2012 Dec. 28; 1:87); for the SFRP2 gene in the tissue, the specificity is 99 percent and the sensitivity is 89.5 percent for colorectal cancer (Nat Genet. 2002 June; 31(2): 141-9), but in the excrement, the specificity is reduced to 77 percent, and the sensitivity is reduced to 77 percent (Lancet. 2004 Apr. 17; 363(9417): 1283-5).

Therefore, the molecular detection of an excrement sample is hardly applied to clinical detection.

SUMMARY OF THE INVENTION

The present invention aims at screening out a tumor marker, of which the detection sensitivity in excrement is not lower than that in tissue.

To achieve the above-mentioned objective, the present invention provides the following technical solution:
the present invention further aims at providing a tumor molecular detection/diagnostic reagent taking excrement as a detection sample. The tumor molecular detection/diagnostic reagent can perform molecular detection/diagnosis on colorectal cancer or precancerous adenoma, and can still obtain extremely high sensitivity and specificity even it takes the excrement as the detection sample.

In the present invention, a molecular marker is firstly screened out. The difference between the molecular marker and other molecular markers is that the detection amount of this molecular marker in the excrement has an extremely high corresponding relation to colorectal cancer. The sensitivity and the specificity of a detection result of the molecular marker in the excrement are even not lower than those of a detection result in a tissue sample.

The present invention provides a colorectal cancer molecular detection/diagnostic reagent, which is characterized in that excrement is used as a detection sample, and an SDC2 gene methylation detection reagent is included.

This special molecular marker screened out by the present invention is SDC2 gene.

The SDC2 gene is a known protein which participates in cell division and migration and is expressed in colonic mesenchymal cells. It is found that the methylation level of target area of SDC2 in a tumor tissue is obviously higher than in paired adjacent non-tumor tissues. By analysis of the methylation levels of SDC2 in primary tumor tissue samples and paired adjacent non-tumor tissue samples of 133 CRC (colorectal cancer) patients, researchers have found that in transcriptional control areas of the SDC2 genes, the methylation levels shown by the tumor tissue samples are obviously higher than those shown by the contrast adjacent non-tumor tissue samples.

Methylation occurs in relatively constant sites of the SDC2 gene, and mostly occurs in CpG island of a promoter region. At the present, most of the common SDC2 gene methylation detection methods are methylation detection for fixed sites of CpG island.

The methylation denotes the addition of a methyl group on cytosine. After being treated with hydrosulphite, the cytosine will become uracil. As similar to thymine, the uracil would be recognized as thymine during PCR (polymerase chain reaction) amplification, which lies in that on a PCR amplification sequence, non-methylated cytosine becomes thymine (C becomes T), and methylated cytosine (C) has no changes. The technology for detecting methylated genes through PCR is generally MSP (methylation-specific PCR): a primer is designed for a treated methylated fragment (namely non-changed C in this fragment) for PCR amplification. If the primer is amplified, there is methylation, and vice versa.

The methylation level of the SDC2 gene in tissue has an extremely high relevancy to attack of the colorectal cancer. The methylation detection rates of the SDC2 genes in 139 tissues are 97.8 percent. When the specificity during blood detection of 131 intestinal cancer patients and 125 normal patients is 95.2 percent, the sensitivity is 87 percent (Oh, T., et al. The Journal of Molecular Diagnostics, 2013). It is unexpected for the inventor that the methylation level of the SDC2 gene detected in the excrement also keeps extremely high relevancy to the attack of the colorectal cancer, with the sensitivity of 87 percent and the specificity which is up to 98 percent and even higher than that in the tissue. This phenomenon is rare, and is the only one in molecular markers.

In comparison with the detection sensitivity or specificity in the tissue sample, the detection sensitivity or specificity of all molecular markers researched by the inventor in the excrement sample are substantially reduced without exception. For example, for the NDRG4 gene, which is a colorectal cancer molecular marker, its detection sensitivity is 81 percent in the tissue, but is reduced to 65.2 percent in the excrement; for the BMP3 gene, its detection sensitivity is 66 percent in the tissue, but is reduced to 39.0 percent in the excrement; and for the Septin9 gene, its detection specificity is 90 percent in the tissue, but is reduced to 43 percent in the excrement. This research shows that various intestinal cancer markers show high detection sensitivity and specificity only in the tissue; while in the excrement sample, although tremendous treatment methods and detection primers have been designed and optimized to try to detect those markers, sensitivities or the specificities are still substantially reduced, which seriously affects the diagnosis of the intestinal cancer.

The SDC2 gene still keeps high sensitivity up to 87 percent and high specificity up to 98 percent in the excrement sample, so that it is extremely particularly used as a reliable intestinal cancer marker in the excrement sample.

Further, the present invention provides a method favorable for extracting and detecting the SDC2 gene in excrement.

A magnetic bead capturing method is implemented by taking magnetic beads as solid phase adsorption carriers and using a specially designed reagent system and extraction procedures (Journal of China Medical University applies the magnetic bead method to detect and extract free methylated DNA in urine; 2015, (10)).

A magnetic bead capturing sequence may be designed for the SDC2 gene. In this present invention, a provided exemplar capturing sequence is as shown in SEQ ID NO: 1 or SEQ ID NO: 2. The SDC2 gene in the excrement may be extracted and gathered through the magnetic bead capturing method.

Optionally, an excrement treatment method is as follows: uniformly mixing and centrifugating excrement in a buffer solution, taking supernate, putting it into another test tube, adding magnetic beads with capturing probes that having specific complementary oligonucleotides (for example, preferred SEQ ID NO: 1: AGCCCGCGCACACGAATCCG-GAGCAGAGTACCG) into the supernage, performing incubation and hybridization, attracting the magnetic beads to one side of the tube wall by a magnet, repeatedly washing the magnetic beads, and then eluting DNA of the target gene by the buffer solution. This method can capture the target gene, with a 2-hour gathering process.

After being treated and modified by bisulfite, the captured DNA is used for subsequent fluorescent quantitation PCR detection.

Further, the present invention designs primers and probes for CpG islands of methylation-prone and constant promoter regions. Exemplar primers are as shown in SEQ ID NO: 3 and SEQ ID NO: 4; or SEQ ID NO: 5 and SEQ ID NO: 6;

or SEQ ID NO: 7 and SEQ ID NO: 8; or SEQ ID NO: 9 and SEQ ID NO: 10; or SEQ ID NO: 11 and SEQ ID NO: 12; or SEQ ID NO: 13 and SEQ ID NO: 14; or SEQ ID NO: 15 and SEQ ID NO: 16; or SEQ ID NO: 17 and SEQ ID NO: 18; or SEQ ID NO: 19 and SEQ ID NO: 20; or SEQ ID NO: 21 and SEQ ID NO: 22; or SEQ ID NO: 23 and SEQ ID NO: 24.

In one preferred embodiment, the adopted primers are SEQ ID NO: 3 and SEQ ID NO: 4.

For the purpose of facilitating showing of results, a detection probe is designed in this present invention. An exemplar probe sequence is as shown in SEQ ID NO: 25 or SEQ ID NO: 26. In one preferred embodiment, the probe sequence is as shown in SEQ ID NO: 26.

The present invention further provides a tumor detection/diagnostic kit, including the detection/diagnostic reagent. Preferably, the tumor is intestinal cancer or precancerous adenoma.

More preferably, the intestinal cancer is colorectal cancer.

The present invention further provides a tumor detection method which takes excrement as a detection sample. The detection sample is mixed with the detection/diagnostic reagent provided by the present invention, and then the mixture is subjected to extraction and amplification; and a detection result is obtained according to an amplification result.

In some specific implementation solutions of the present invention, the object of amplification in the detection method is a tumor marker which is selected from the SDC2 gene, the NDRG4 gene, the BMP3 gene or the Septin9 gene.

In some specific implementation solutions of the present invention, the detection result is obtained in the detection method by comparing an amplification result of a sample to be detected with an amplification result of a normal sample. If the amplification results of the sample to be detected and the normal sample have a significant difference or an extremely significant difference, the result for a donor of the sample to be detected is positive.

Compared with the prior art, the present invention has the following beneficial effects:

1. The colorectal cancer diagnostic reagent provided by the invention can simply make reliable diagnosis on the colorectal cancer by taking the excrement as the detection sample. As a detection sample used in the present invention, the excrement of a patient is very easy to obtain, and it will not cause any pain and inconvenience to the patient. A bit of sample is used, and the sampling process is very convenient and has no influence on the patient. In addition, the sample is convenient to post or may be taken to the hospital conveniently for detection.

2. The present invention can simultaneously find the tumors on the left and right side colons, does not have detection blind areas possibly caused in other conventional methods, and can find both the intestinal cancer and the precancerous adenoma, rendering it possible to prevent the intestinal cancer by excising the precancerous adenoma.

3. The reagent/kit provided by the present invention detects and diagnoses cancers on the basis of the methylation level. More and more researches verify that methylation changes are early events of tumorigenesis, and detecting abnormal methylation may find out early lesions more easily.

4. The present invention takes the excrement as the detection sample, and includes the SDC2 gene methylation detection reagent. The detected methylation level of the SDC2 gene in the excrement also keeps extremely high relevancy to the attack of the colorectal cancer, with the sensitivity of 87 percent, and the specificity which is up to 98 percent and even higher than that in the tissue.

BRIEF DESCRIPTION OF THE DRAWINGS

FIGS. 1A and 1B depict an ROC (receiver operating characteristic) curve of detecting colorectal cancer (A) and precancerous adenoma (polypus having a diameter more than or equal to 1 cm) (B) based on the SDC2 gene;

FIGS. 2A and 2B depict an ROC curve of detecting colorectal cancer (A) and precancerous adenoma (polypus having a diameter more than or equal to 1 cm) (B) based on the NDRG4 gene;

DETAILED DESCRIPTION OF THE INVENTION

Figure 3A:
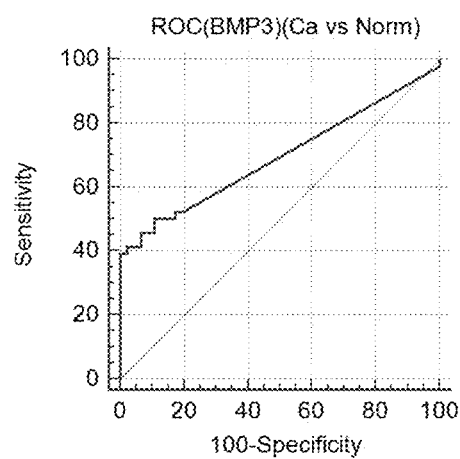
FIGS. 3A and 3B depict an ROC curve of detecting colorectal cancer (A) and precancerous adenoma (polypus having a diameter more than or equal to 1 cm) (B) based on the BMP3 gene.

The present invention discloses a tumor molecular detection/diagnostic reagent. A person skilled in the art can make proper improvements on process parameters by referring to contents in this text. It should be particularly noted that it is evident for the person skilled in the art to make all similar replacements and changes that shall all be deemed as being included in the present invention. The method and application of the present invention have been described by means of preferred embodiments, and it is obvious for relevant persons to make changes or proper alterations and combinations to the method and application described in this text without departing from the contents, spirit and scope of the present invention to implement and apply the technologies of the present invention.

Raw materials and reagents which are used in the tumor molecular detection/diagnostic reagent provided by the present invention may be all purchased on the market.

A further description will be made to the technical solution of the present invention by specific embodiments, and the specific embodiments are not representative of limitations to the scope of protection of the present invention. Some nonessential modifications and adjustments that are made by others according to the theory of the present invention shall still fall within the scope of protection of the present invention.

Embodiment 1 Sample Treatment and DNA Extraction

An excrement sample and a buffer solution are mixed and ground according to a ratio of 1 g of excrement to 4 ml of buffer solution, and then the mixture is centrifugated so as to reserve supernate and abandon precipitates.

8 ml of the supernate is centrifugated at 4000 rpm for 5 min, and then 5 ml of the centrifugated supernate is transferred into a new centrifugal tube which is pre-filled with 3 ml of cell lysis buffer and has the volume of 15 ml.

100 ul of capturing magnetic beads are added into each centrifugal tubes which are incubated in a water bath kettle at 92 DEG C. for 10 min and incubated in a table concentrator at 100 rpm at room temperature for 1 h, and then after short centrifugation, the centrifugal tubes are placed on a magnetic frame for 5 min so as to abandon the supernate.

There are two available capturing probes, which are both effective and can capture target fragments.

```
Capturing probe 1:
SEQ ID NO. 1:    AGCCCGCGCACACGAATCCGGAGCAGAGTACCG

Capturing probe 2:
SEQ ID NO. 2:    CTCCTGCCCAGCGCTCGGCGCAGCCCGC
```

500 ul of a cleaning solution is added into the centrifugal tube having the volume of 15 ml, and then the centrifugal tube is shaken for uniform mixing to enable the magnetic beads on the tube wall to be suspended completely; and after short centrifugation, the solution is transferred into a new centrifugal tube having the volume of 2 ml. The centrifugal tube is incubated in a dry bath incubator at 900 rpm at room temperature for 1 min, and then is placed on the magnetic frame for 1 min so as to abandon the supernate. The above-mentioned operation is repeated for 4 times.

55 ul of eluent is added, and after short centrifugation, the centrifugal tube is incubated in the dry bath incubator at 900 rpm at 92 DEG C. for 10 min. After short centrifugation, the centrifugal tube is placed on the magnetic frame, and 50 ul of eluent is transferred into a new EP tube within 3 min.

A DNA fragment in the step 6 is methylated with an EZ methylation kit (a product of the Zymo Research Company), and a final sample is subjected to PCR detection.

Analysis of the capturing efficiency of the capturing probes:

The two capturing probes are used for capturing the same sample, and the concentrations of the captured DNA fragments are measured through an ultraviolet spectrophotometer, obtaining results as follows:

| Used probe | OD260 | Concentration of DNA (ng/uL) (50(ng/uL) × OD260) |
|---|---|---|
| SEQ ID NO. 1 | 1.9 | 95 |
| SEQ ID NO. 2 | 1.7 | 85 |

The two probes can capture the target fragments. The effect of SEQ ID NO: 1 is better than that of SEQ ID NO: 2, the optimal experiment adopts the probes.

Embodiment 2 PCR (Polymerase Chain Reaction) Detection Process

A PCR system and procedures are respectively as shown in Table 1 and Table 2.

TABLE 1

| PCR system | |
|---|---|
| Component | Adding amount (ul) |
| Forward primer (FP) (100 uM) | 0.125 |
| Backward primer (RP) (100 uM) | 0.125 |
| Probe (100 uM) | 0.05 |
| dNTP (10 mM) | 1 |
| Magnesium ion | 5 |
| 5*buffer | 5 |
| Reaction enzyme | 0.5 |
| Nuclease-free water | 8.2 |
| DNA to be detected | 5 |
| Total | 25 |

TABLE 2

| PCR procedures | | |
|---|---|---|
| Cycle number | Temperature (° C.) | Time (s) |
| 1 | 95 | 300 |
| 10 | 95 | 20 |
|  | 62 | 30 |
|  | 70 | 30 |
| 40 | 95 | 20 |
|  | 58 | 60 |
|  | 72 | 30 (Collection of fluorescence) |
| 1 | 37 | 30 |

Primers are designed, and their amplification efficiency is researched (as shown in Table 3). The amplification system and the procedures are as mentioned above.

TABLE 3

Primers and amplification efficiency

Figure 5:
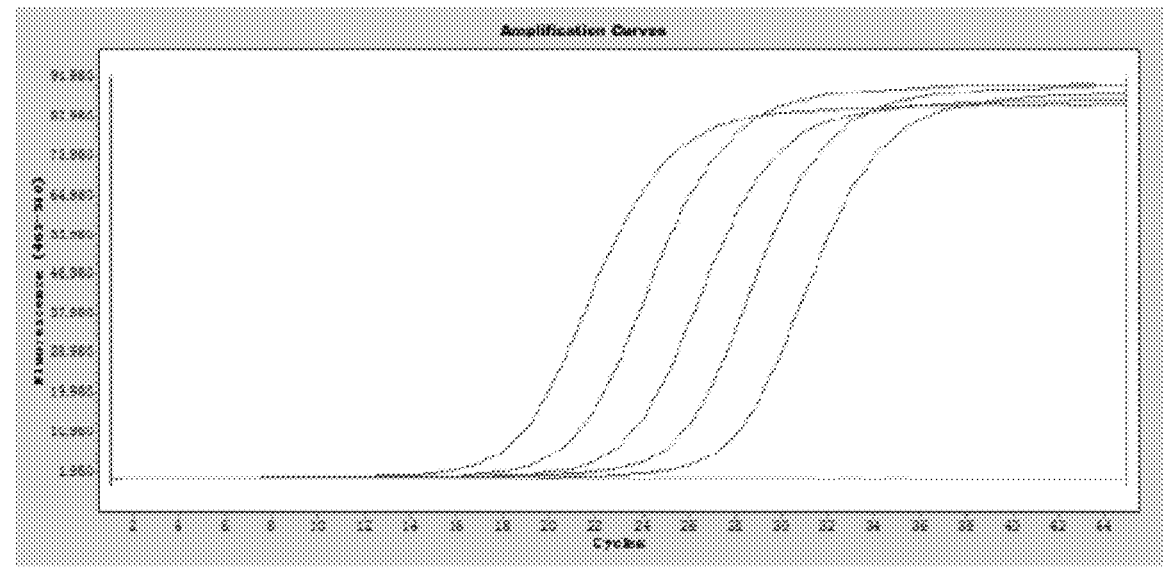
FIGS. 5 to 15 are amplification curves of primers SM-0 to SM-10, successively.
Figure 6:
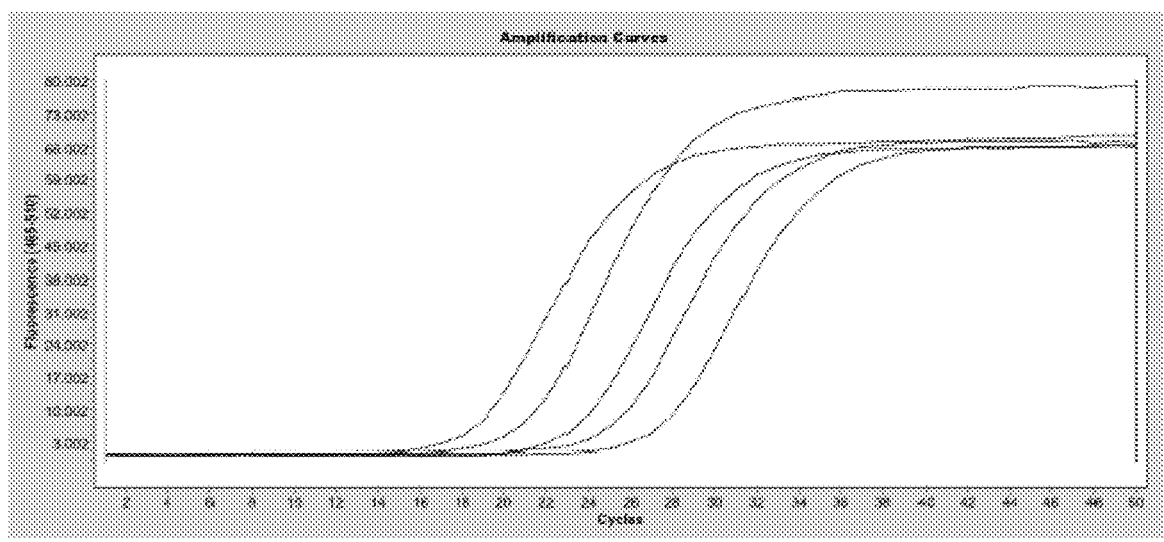
Figure 7:
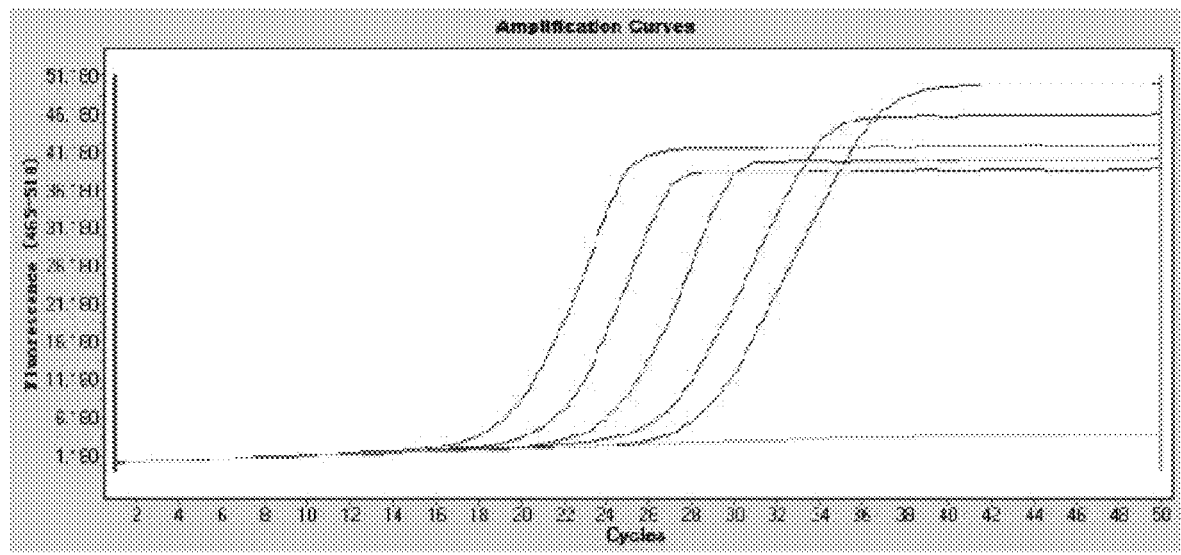
Figure 8:
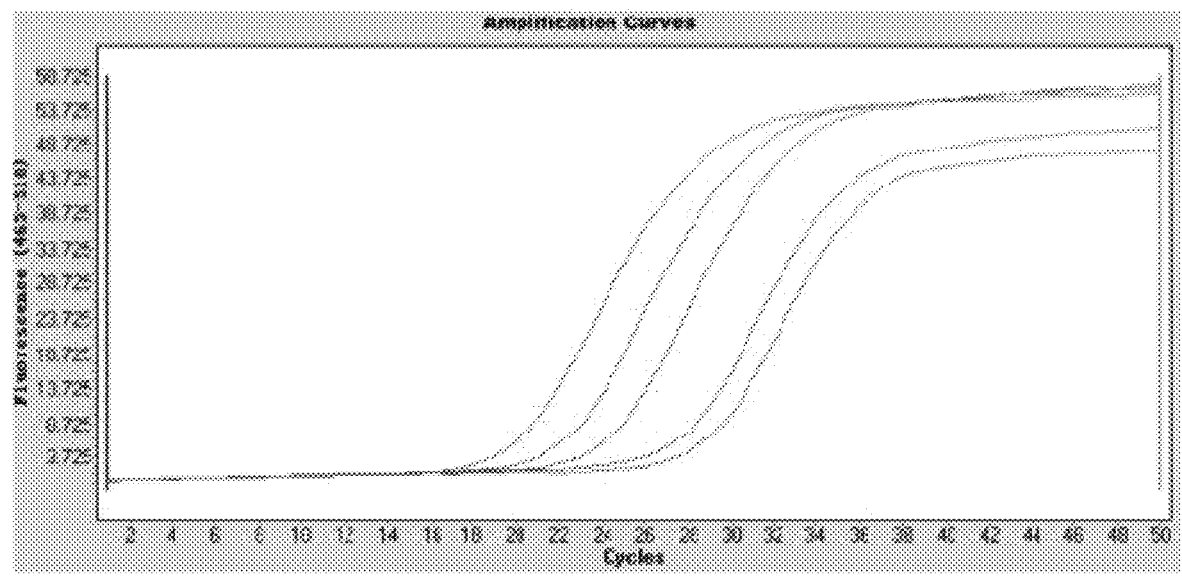
Figure 9:
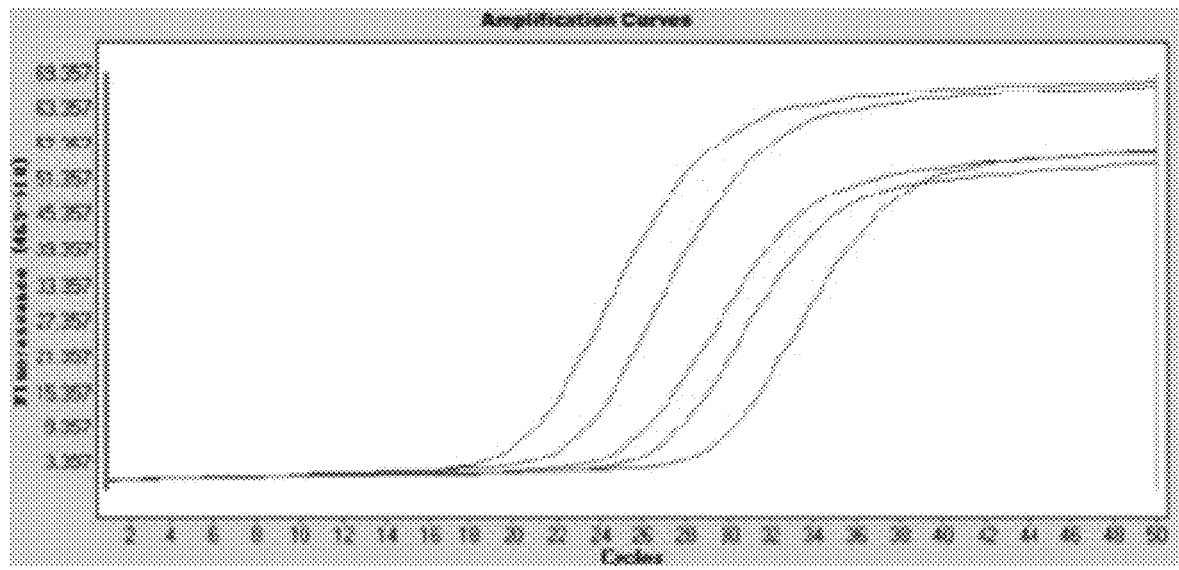

| Sequence number | Primer name | Sequence | Amplification result |
|---|---|---|---|
| SEQ ID NO. 3 | SM-0FP | GAGGAAGCGAGCGTTTTC | FIG. 5 |
| SEQ ID NO. 4 | SM-0RP | AAAATACCGCAACGATTACGA | |
| SEQ ID NO. 5 | SM-1FP | GTAGGAGGAGGAAGCGAGCGTTTTC | FIG. 6 |
| SEQ ID NO. 6 | SM-1RP | CGCAACGATTACGACTCAAACTCGA | |
| SEQ ID NO. 7 | SM-2FP | TAGGAGGAGGAAGTGAGTGTTTTG | FIG. 7 |
| SEQ ID NO. 8 | SM-2RP | ACCACAACAATTACAACTCAAACTCAA | |
| SEQ ID NO. 9 | SM-3FP | GTAGGAGGAGGAAGCGAGCGTTTTC | FIG. 8 |
| SEQ ID NO. 10 | SM-3RP | CCGCAACGATTACGACTCAAACTCG | |
| SEQ ID NO. 11 | SM-4FP | TAGGAGGAGGAAGTGAGTGTTTTG | FIG. 9 |
| SEQ ID NO. 12 | SM-4RP | ACCACAACAATTACAACTCAAACTCAA | |

TABLE 3-continued

Primers and amplification efficiency

Figure 10:
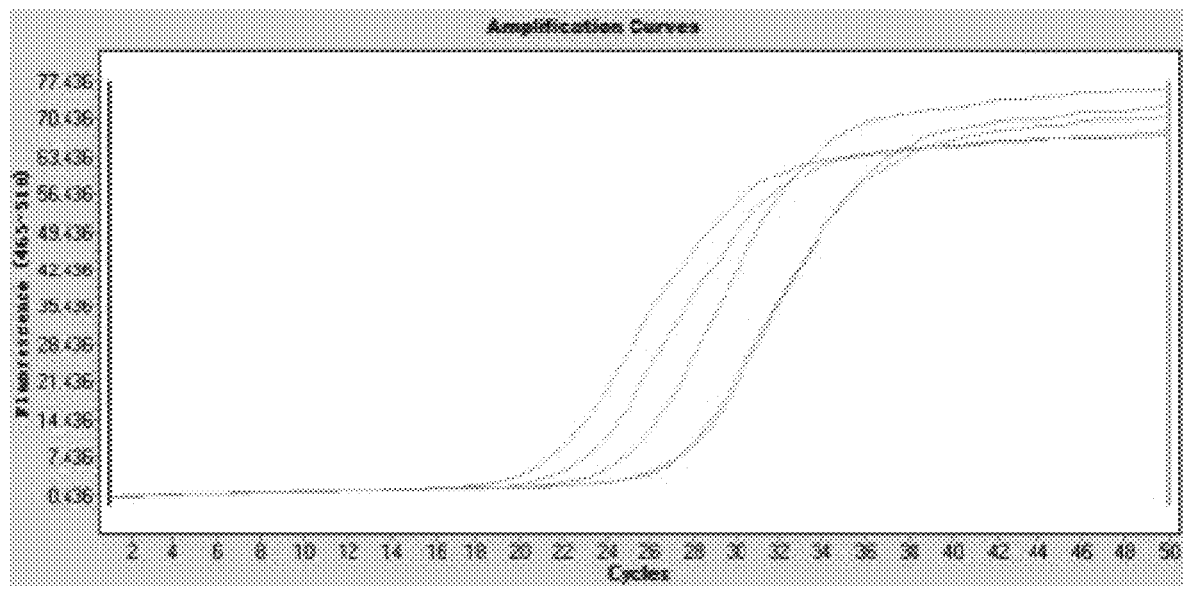
Figure 11:
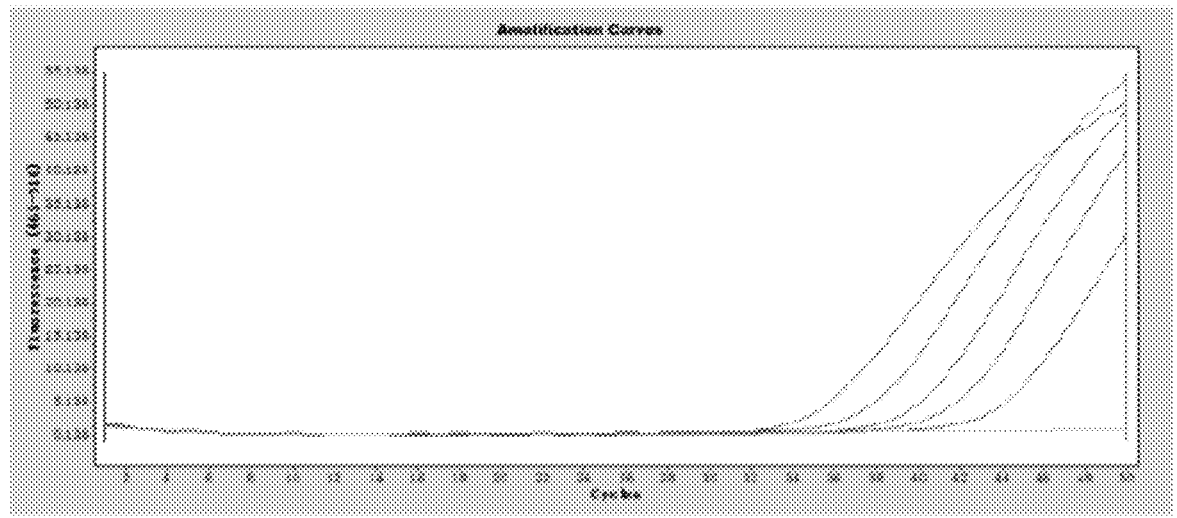
Figure 12:
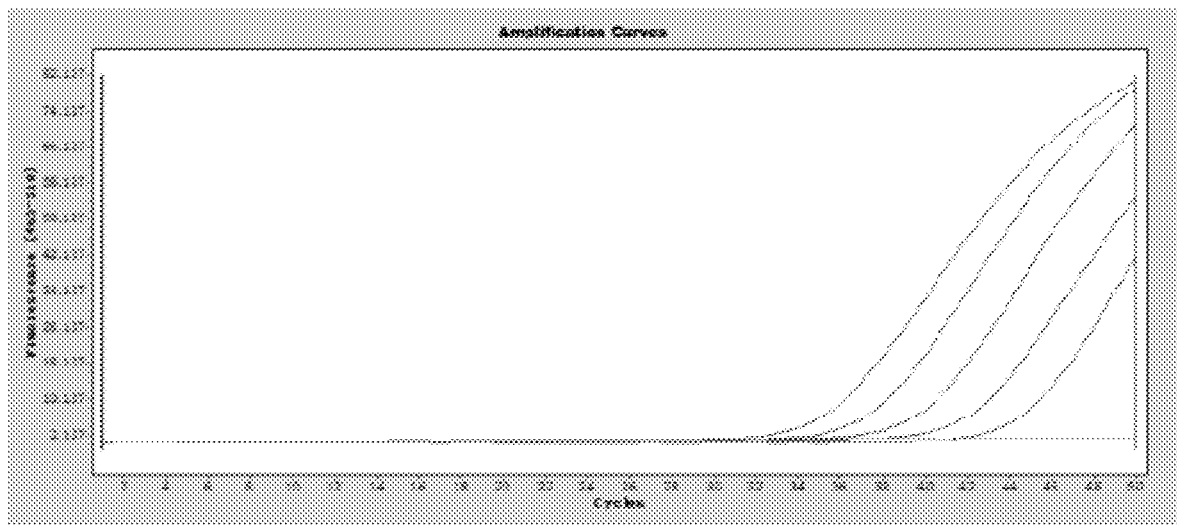
Figure 13:
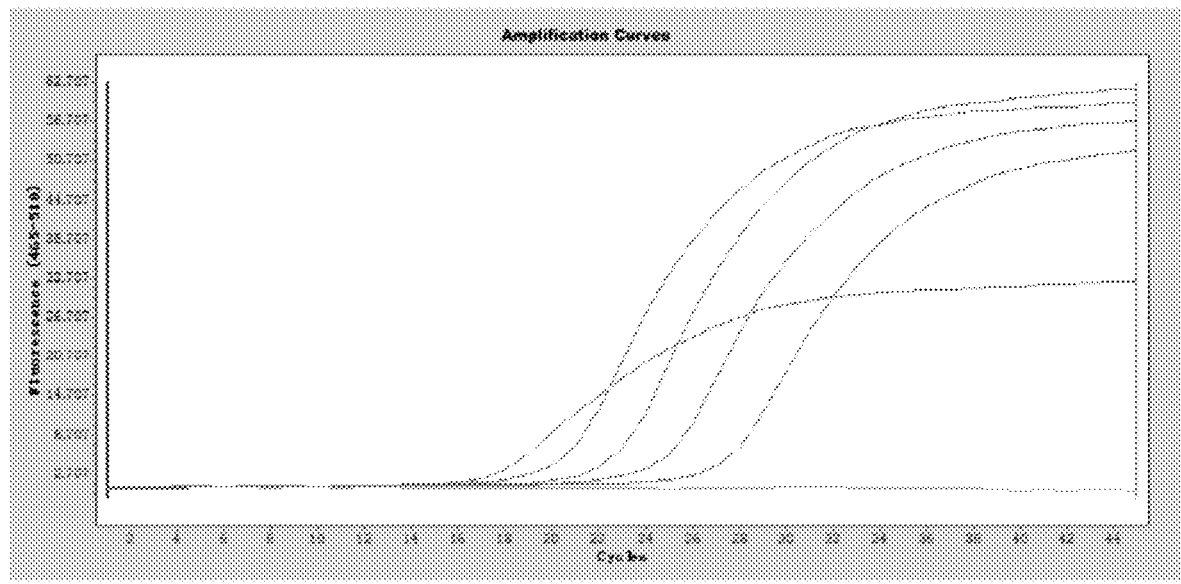
Figure 14:
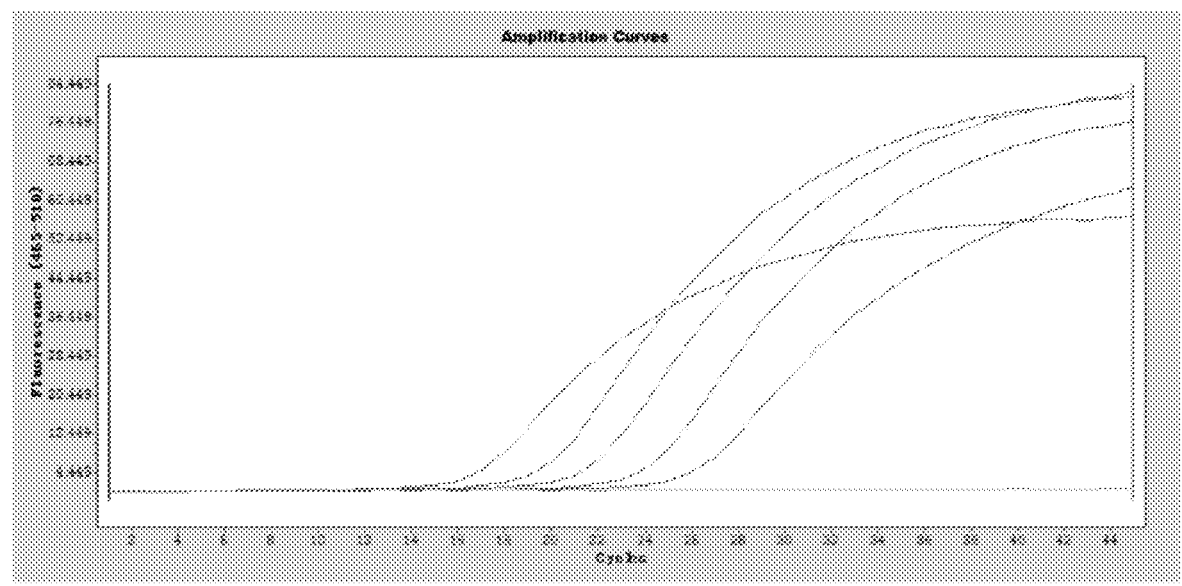
Figure 15:
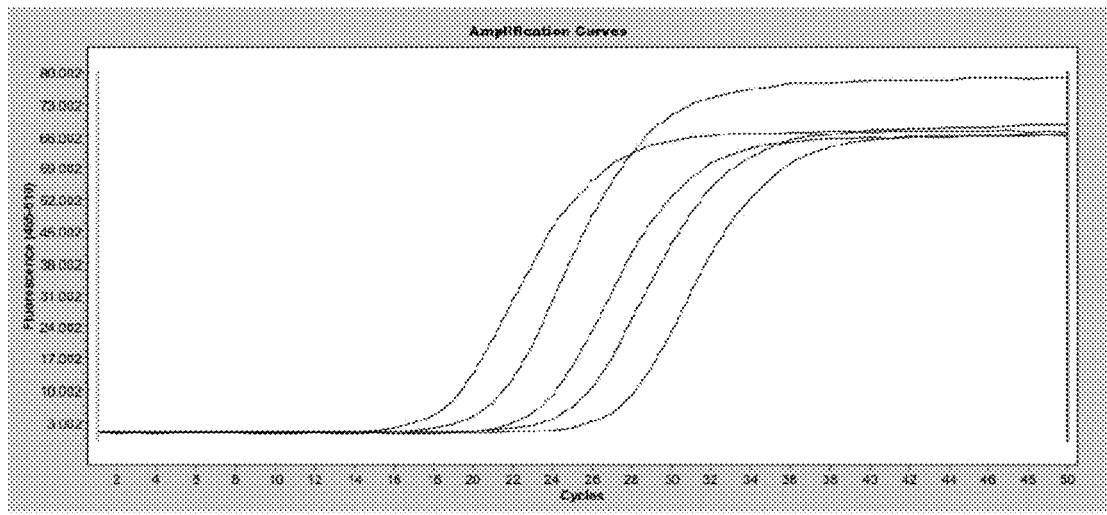

| Sequence number | Primer name | Sequence | Amplification result |
|---|---|---|---|
| SEQ ID NO. 13 | SM-5FP | GTAGGAGGAGGAAGCGAGCGTTTTC | FIG. 10 |
| SEQ ID NO. 14 | SM-5RP | CGCAACGATTACGACTCAAACTCGA | |
| SEQ ID NO. 15 | SM-6FP | TAGGAGGAGGAAGTGAGTGTTTTTG | FIG. 11 |
| SEQ ID NO. 16 | SM-6RP | CCACAACAATTACAACTCAAACTCAA | |
| SEQ ID NO. 17 | SM-7FP | GTAGGAGGAGGAAGCGAGCGTTTTC | FIG. 12 |
| SEQ ID NO. 18 | SM-7RP | CCGCAACGATTACGACTCAAACTCG | |
| SEQ ID NO. 19 | SM-8FP | TAGGAGGAGGAAGTGAGTGTTTTTG | FIG. 13 |
| SEQ ID NO. 20 | SM-8RP | CCACAACAATTACAACTCAAACTCAA | |
| SEQ ID NO. 21 | SM-9FP | GTAGGAGGAGGAAGCGAGCGTTTTC | FIG. 14 |
| SEQ ID NO. 22 | SM-9RP | CGCAACGATTACGACTCAAACTCGA | |
| SEQ ID NO. 23 | SM-10FP | GTAGGAGGAGGAAGTGAGTGTTTTTG | FIG. 15 |
| SEQ ID NO. 24 | SM-10RP | ACCACAACAATTACAACTCAAACTCAA | |

The PCR results of the primers are respectively as shown in FIGS. 5 to 15. It can be seen from the results that the primers SEQ ID NO: 3 and SEQ ID NO: 4 have the highest amplification efficiency.

The primer pair of SEQ ID NO: 3 and SEQ ID NO: 4, which has the highest amplification efficiency, is used.

The detection probes are further designed. Optimized detection probe examples are as follows.

Probe 1: SEQ ID NO. 25:
AGTTTCGAGTTCGAGTTTTCGAGTTTG

Probe 2: SEQ ID NO. 26:
CAAACTCGAAAACTCGAACTCGAAACT

Ten holes are repeated. The experiment is performed twice. The PCR system and procedures are as shown in Table 1 and Table 2.

Figure 16:
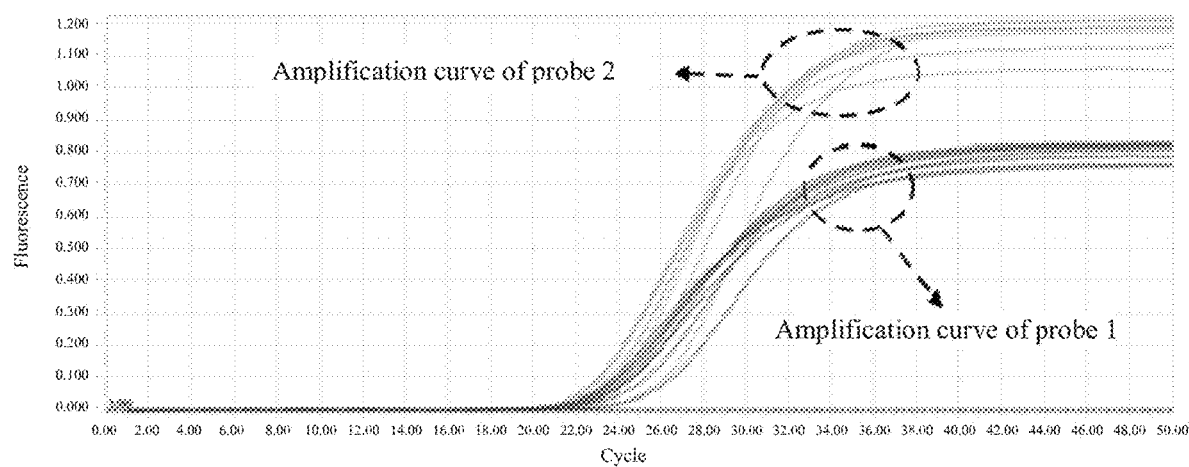
FIG. 16 is a fluorescent PCR detection result (probe 1)
Figure 17:
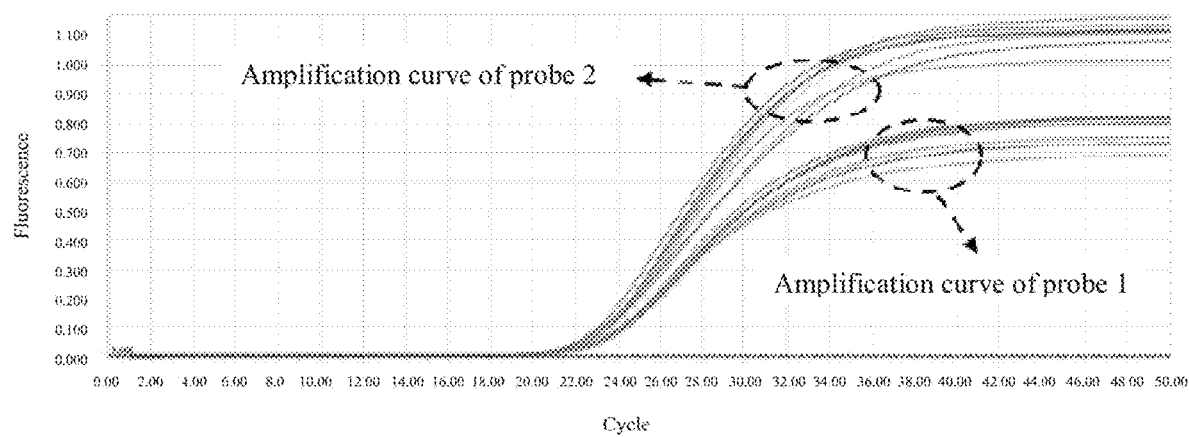
FIG. 17 is a fluorescent PCR detection result (probe 2).

Fluorescence curves of the probe 1 and probe 2 are respectively as shown in FIG. 16 and FIG. 17.

It can be seen from the results that the probe 1 and the probe 2 can ensure that the PCR process is performed normally. By contrast, a fluorescence value obtained by the probe 2 is higher, and is more favorable for the judgment on the result, particularly for the judgment on a positive sample.

The probe 2 is adopted to detect the sample in the optimal experiment.

Embodiment 3 Sample Detection

Excrement samples of 46 patients definitely diagnosed as suffering from intestinal cancer based on enteroscopy and pathological examination, excrement samples of 46 patients definitely diagnosed as suffering from precancerous adenoma (polypus having a diameter more than or equal to 1 cm) based on enteroscopy and pathological examination, and excrement samples of 46 patients definitely diagnosed as normal based on enteroscopy were clinically collected.

The above-mentioned excrement samples were treated and subjected to DNA extraction according to the method in Embodiment 1. The 138 samples were subjected to PCR detection by using the PCR detection process in Embodiment 2.

The 46 intestinal cancer patients (Ca) (definitely diagnosed as suffering from the intestinal cancer based on the enteroscopy), the 46 normal patients (Norm) (definitely diagnosed as normal based on the enteroscopy), and the 46 precancerous adenoma patients (polypus having a diameter more than or equal to 1 cm, LA, definitely diagnosed that the diameter of the polypus is more than or equal to 1 cm based on the enteroscopy) were detected.

Data were processed and analyzed by using MedCalc software.

Results are as shown in FIGS. 1A and 1B, and in FIGS. 2A and 2B.

FIG. 1A is an ROC (receiver operating characteristic) curve of detecting the colorectal cancer based on the SDC2 gene, and FIG. 1B is an ROC curve of detecting the precancerous adenoma (polypus having a diameter more than or equal to 1 cm) based on the SDC2 gene.

For the colorectal cancer, the detection sensitivity of the SDC2 gene is 87 percent, and the specificity is 98 percent. The area under the receiver curve is 0.953.

For the precancerous adenoma (polypus having a diameter more than or equal to 1 cm), the detection sensitivity of the SDC2 gene is 73 percent, and the specificity is 96 percent. The area under the receiver curve is 0.882.

Embodiment 4 Detection Results of Other Exemplar Molecular Markers

In a process of exploring the technical solution of the present invention, the inventor had explored various intestinal cancer markers.

With reference to the system design methods of Embodiment 1, 2 and 3, excrement detection for the NDRG4 gene, the BMP3 gene and the Septin9 gene was explored in the present invention.

After the optimal detection method was performed on those genes respectively, the clinically samples in Embodiment 3 were analyzed in the same way.

Results obtained by detecting the colorectal cancer and the precancerous adenoma based on the NDRG4 gene are as shown in FIGS. 2A and 2B.

FIG. 2A is an ROC curve of detecting the colorectal cancer based on the NDRG4 gene, and FIG. 2B is an ROC curve of detecting the precancerous adenoma (polypus having a diameter more than or equal to 1 cm) based on the NDRG4 gene.

For the colorectal cancer, the detection sensitivity of the NDRG4 gene is 65.2 percent, and the specificity is 97.8 percent. The area under the receiver curve is 0.826.

For the precancerous adenoma (polypus having a diameter more than or equal to 1 cm), the detection sensitivity of the NDRG4 gene is 45.7 percent, and the specificity is 97.8 percent. The area under the receiver curve is 0.694.

Figure 3B:
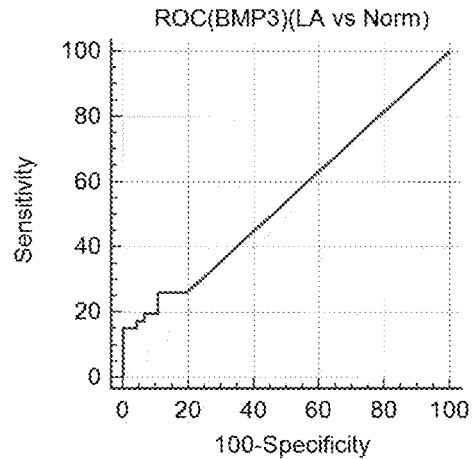

Results obtained by detecting the colorectal cancer and the precancerous adenoma based on the BMP3 gene are as shown in FIGS. 3A and 3B.

FIG. 3A is an ROC curve of detecting the colorectal cancer based on the BMP3 gene, and FIG. 3B is an ROC curve of detecting the precancerous adenoma (polypus having a diameter more than or equal to 1 cm) based on the BMP3 gene.

For the colorectal cancer, the detection sensitivity of the BMP3 gene is 50.0 percent, and the specificity is 89.1 percent. The area under the receiver curve is 0.694.

For the precancerous adenoma (polypus having a diameter more than or equal to 1 cm), the detection sensitivity of the BMP3 gene is 26.1 percent, and the specificity is 89.1 percent. The area under the receiver curve is 0.549.

Figure 4A:
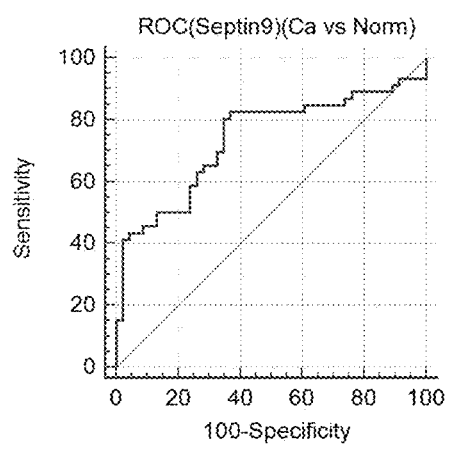
FIGS. 4A and 4B depict an ROC curve of detecting colorectal cancer (A) and precancerous adenoma (polypus having a diameter more than or equal to 1 cm) (B) based on the Septin9 gene.
Figure 4B:
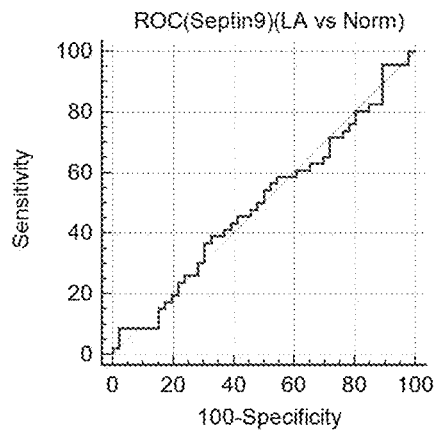

Results obtained by detecting the colorectal cancer and the precancerous adenoma based on the Septin9 gene are as shown in FIGS. 4A and 4B.

FIG. 4A is an ROC curve of detecting the colorectal cancer based on the Septin9 gene, and FIG. 4B is an ROC curve of detecting the precancerous adenoma (polypus having a diameter more than or equal to 1 cm) based on the Septin9 gene.

For the colorectal cancer, the detection sensitivity of the Septin9 gene is 82.6 percent, and the specificity is 63.0 percent. The area under the receiver curve is 0.737.

For the precancerous adenoma (polypus having a diameter more than or equal to 1 cm), the detection sensitivity of the Septin9 gene is 13.0 percent, and the specificity is 97.8 percent. The area under the receiver curve is 0.534.

The above-mentioned embodiments are only preferred implementation modes of the present invention, but not intended to limit the implementation modes of the present invention. Any other changes, modifications, replacements, combinations and simplifications that are made without departing from the spirit and theory of the present invention shall all fall within the scope of protection of the present invention.

The above detailed description is made to the tumor molecular detection/diagnostic reagent provided by the present invention. In this text, specific cases are applied to describe the principle and implementation modes of the present invention, and descriptions of the above embodiments are only used for assisting in understanding the method of the present invention and its main idea.

It should be noted that a person skilled in the art further can make a plurality of improvements and modifications to the present invention without departing from the theory of the present invention, and these improvements and modifications shall also fall within the scope of protection of claims of the present invention.

The invention claimed is:

1. A tumor molecular detection/diagnostic reagent comprising an SDC2 gene methylation detection reagent,
   wherein the SDC2 gene methylation detection reagent contains a first amplification primer and a second amplification primer, and
   wherein said first amplification primer consists of the nucleotide sequence of SEQ ID NO: 3 and said second amplification primer consists of the nucleotide sequence of SEQ ID NO: 4.

2. The detection/diagnostic reagent according to claim 1, wherein said tumor molecular detection/diagnostic reagent further comprises DNA capturing reagents.

3. The detection/diagnostic reagent according to claim 2, wherein the DNA capturing reagents are capturing magnetic beads.

4. The detection/diagnostic reagent according to claim 3, wherein the capturing magnetic beads comprise a capturing sequence for the SDC2 gene.

5. The detection/diagnostic reagent according to claim 4, wherein the capturing sequence is selected from the group consisting of SEQ ID NO: 1 and SEQ ID NO: 2.

6. The detection/diagnostic reagent according to claim 3, wherein the capturing magnetic beads comprise a capturing for a CpG island of the SDC2 gene.

7. The detection/diagnostic reagent according to claim 1, wherein the SDC2 gene methylation detection reagent is a methylation detection reagent for a CpG island.

8. The detection/diagnostic reagent according to claim 1, wherein said detection/diagnostic reagent further comprises a detection probe.

9. The detection/diagnostic reagent according to claim 8, wherein the detection probe has a sequence selected from the group consisting of SEQ ID NO: 25 and SEQ ID NO: 26.

10. The detection/diagnostic reagent according to claim 1, wherein the tumor is intestinal cancer or precancerous adenoma.

11. The detection/diagnostic reagent according to claim 10, wherein the intestinal cancer is colorectal cancer.

12. A tumor detection/diagnostic kit, comprising the detection/diagnostic reagent according to claim 1.

13. The tumor detection/diagnostic kit according to claim 12, wherein the tumor is intestinal cancer or precancerous adenoma.

14. The tumor detection/diagnostic kit according to claim 13, wherein the intestinal cancer is colorectal cancer.

15. A method of detecting an intestinal tumor in a human subject comprising:
   obtaining a sample of excrement from a human subject;
   extracting DNA from said sample of excrement;
   amplifying the DNA using the tumor molecular detection/diagnostic reagent of claim 1; and
   detecting the presence of an intestinal tumor in the human subject when the level of the amplification product is greater in comparison to the level of an amplification product in control excrement samples from human subjects that do not have intestinal tumors.

* * * * *

SEQUENCE LISTING

<160> NUMBER OF SEQ ID NOS: 26

<210> SEQ ID NO 1
<211> LENGTH: 33
<212> TYPE: DNA
<213> ORGANISM: Artificial Sequence
<220> FEATURE:
<223> OTHER INFORMATION: Synthetic oligonucleotide sequence

<400> SEQUENCE: 1
agcccgcgca cacgaatccg gagcagagta ccg                             33

<210> SEQ ID NO 2
<211> LENGTH: 28
<212> TYPE: DNA
<213> ORGANISM: Artificial Sequence
<220> FEATURE:
<223> OTHER INFORMATION: Synthetic oligonucleotide sequence

<400> SEQUENCE: 2
ctcctgccca gcgctcggcg cagcccgc                                   28

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 3
gaggaagcga gcgttttc                                              18

<210> SEQ ID NO 4
<211> LENGTH: 21
<212> TYPE: DNA

```
<213> ORGANISM: Artificial Sequence
<220> FEATURE:
<223> OTHER INFORMATION: Synthetic oligonucleotide sequence

<400> SEQUENCE: 4
aaaataccgc aacgattacg a                                             21

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 5
gtaggaggag gaagcgagcg ttttc                                         25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 6
cgcaacgatt acgactcaaa ctcga                                         25

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 7
taggaggagg aagtgagtgt ttttg                                         25

<210> SEQ ID NO 8
<211> LENGTH: 27
<212> TYPE: DNA
<213> ORGANISM: Artificial Sequence
<220> FEATURE:
<223> OTHER INFORMATION: Synthetic oligonucleotide sequence

<400> SEQUENCE: 8
accacaacaa ttacaactca aactcaa                                       27

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 9
gtaggaggag gaagcgagcg ttttc                                         25

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 10
ccgcaacgat tacgactcaa actcg                                         25
```

```
<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 11
taggaggagg aagtgagtgt ttttg                                              25

<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotide sequence

<400> SEQUENCE: 12
accacaacaa ttacaactca aactcaa                                            27

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 13
gtaggaggag gaagcgagcg ttttc                                              25

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 14
cgcaacgatt acgactcaaa ctcga                                              25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 15
taggaggagg aagtgagtgt ttttg                                              25

<210> SEQ ID NO 16
<211> LENGTH: 26
<212> TYPE: DNA
<213> ORGANISM: Artificial Sequence
<220> FEATURE:
<223> OTHER INFORMATION: Synthetic oligonucleotide sequence

<400> SEQUENCE: 16
ccacaacaat tacaactcaa actcaa                                             26

<210> SEQ ID NO 17
<211> LENGTH: 25
<212> TYPE: DNA
<213> ORGANISM: Artificial Sequence
<220> FEATURE:
```

<223> OTHER INFORMATION: Synthetic oligonucleotide sequence

<400> SEQUENCE: 17
gtaggaggag gaagcgagcg ttttc                                              25

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 18
ccgcaacgat tacgactcaa actcg                                              25

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 19
taggaggagg aagtgagtgt ttttg                                              25

<210> SEQ ID NO 20
<211> LENGTH: 26
<212> TYPE: DNA
<213> ORGANISM: Artificial Sequence
<220> FEATURE:
<223> OTHER INFORMATION: Synthetic oligonucleotide sequence

<400> SEQUENCE: 20
ccacaacaat tacaactcaa actcaa                                             26

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 21
gtaggaggag gaagcgagcg ttttc                                              25

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide sequence

<400> SEQUENCE: 22
cgcaacgatt acgactcaaa ctcga                                              25

<210> SEQ ID NO 23
<211> LENGTH: 26
<212> TYPE: DNA
<213> ORGANISM: Artificial Sequence
<220> FEATURE:
<223> OTHER INFORMATION: Synthetic oligonucleotide sequence

<400> SEQUENCE: 23
gtaggaggag gaagtgagtg tttttg                                             26

```
<210> SEQ ID NO 24
<211> LENGTH: 27
<212> TYPE: DNA
<213> ORGANISM: Artificial Sequence
<220> FEATURE:
<223> OTHER INFORMATION: Synthetic oligonucleotide sequence

<400> SEQUENCE: 24
accacaacaa ttacaactca aactcaa                                              27

<210> SEQ ID NO 25
<211> LENGTH: 27
<212> TYPE: DNA
<213> ORGANISM: Artificial Sequence
<220> FEATURE:
<223> OTHER INFORMATION: Synthetic oligonucleotide sequence

<400> SEQUENCE: 25
agtttcgagt tcgagttttc gagtttg                                              27

<210> SEQ ID NO 26
<211> LENGTH: 27
<212> TYPE: DNA
<213> ORGANISM: Artificial Sequence
<220> FEATURE:
<223> OTHER INFORMATION: Synthetic oligonucleotide sequence

<400> SEQUENCE: 26
caaactcgaa aactcgaact cgaaact                                              27
```